(12) United States Patent
Gadikota et al.

(10) Patent No.: US 9,770,323 B2
(45) Date of Patent: Sep. 26, 2017

(54) SINGLE TUNNEL, DOUBLE BUNDLE ANTERIOR CRUCIATE LIGAMENT RECONSTRUCTION USING BONE-PATELLAR TENDON-BONE GRAFTS

(71) Applicant: The General Hospital Corporation, Boston, MA (US)

(72) Inventors: Hemanth R. Gadikota, Boston, MA (US); Thomas J. Gill, Boston, MA (US); Guoan Li, Milton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/690,851

(22) Filed: Apr. 20, 2015

(65) Prior Publication Data
US 2016/0008124 A1    Jan. 14, 2016

Related U.S. Application Data

(62) Division of application No. 13/122,845, filed as application No. PCT/US2009/060466 on Oct. 13, 2009, now Pat. No. 9,011,533.
(Continued)

(51) Int. Cl.
*A61F 2/08* (2006.01)
*A61B 17/04* (2006.01)
(Continued)

(52) U.S. Cl.
CPC ........ *A61F 2/0811* (2013.01); *A61B 17/0401* (2013.01); *A61B 17/686* (2013.01);
(Continued)

(58) Field of Classification Search
CPC ............ A61F 2/08; A61B 17/56; A61B 17/04
(Continued)

(56) References Cited

U.S. PATENT DOCUMENTS 5,603,716 A    2/1997  Morgan et al.
5,683,394 A    11/1997 Rinner
(Continued)

FOREIGN PATENT DOCUMENTS

WO    2005069884 A2    8/2005

OTHER PUBLICATIONS

Aglietti, et al., Long-Term Study of Anterior Cruciate Ligament Reconstruction for Chronic Instability Using the Central One-Third Patellar Tendon and a Lateral Extraarticular Tenodesis, The American Journal of Sports Medicine, 1992, 20(1):38-45.
(Continued)

*Primary Examiner* — Yashita Sharma
(74) *Attorney, Agent, or Firm* — Quarles & Brady LLP

(57) ABSTRACT

Anterior cruciate ligament reconstruction methods and devices are designed to achieve an anatomically accurate double bundle anterior cruciate ligament reconstruction by using a single femoral and tibial tunnel. The method and devices reconstruct the two bundles of the anterior cruciate ligament in a single femoral and tibial tunnel using a bone-patellar tendon-bone graft. The methods and devices enable an accurate anatomical reconstruction of the anteromedial and posterolateral bundles by creating a single femoral and tibial tunnel as opposed to creating two tunnels in the tibia and femur.

13 Claims, 5 Drawing Sheets

Related U.S. Application Data

(60) Provisional application No. 61/104,876, filed on Oct. 13, 2008.

(51) Int. Cl.
*A61B 17/68* (2006.01)
*A61B 17/86* (2006.01)

(52) U.S. Cl.
CPC ..... *A61B 17/863* (2013.01); *A61B 2017/0414* (2013.01); *A61F 2002/087* (2013.01); *A61F 2002/0835* (2013.01); *A61F 2002/0858* (2013.01); *A61F 2002/0882* (2013.01)

(58) Field of Classification Search
USPC ............. 623/13.11–13.2; 606/232, 233, 286, 606/300–301, 310–317
See application file for complete search history.

(56) References Cited

U.S. PATENT DOCUMENTS

| | | | |
|---|---|---|---|
| 5,785,714 | A | 7/1998 | Morgan et al. |
| 5,961,520 | A | 10/1999 | Beck, Jr. et al. |
| 6,203,572 | B1 | 3/2001 | Johnson et al. |
| 6,235,057 | B1 | 5/2001 | Roger et al. |
| 6,537,319 | B2 | 3/2003 | Whelan |
| 6,562,072 | B1 | 5/2003 | Fuss et al. |
| 6,623,524 | B2 | 9/2003 | Schmieding |
| 6,887,271 | B2 | 5/2005 | Justin et al. |
| 6,890,354 | B2 | 5/2005 | Steiner et al. |
| 7,066,956 | B2 | 6/2006 | Schmieding et al. |
| 7,077,863 | B2 | 7/2006 | Schmieding et al. |
| 7,137,996 | B2 | 11/2006 | Steiner et al. |
| 7,141,066 | B2 | 11/2006 | Steiner et al. |
| 7,309,356 | B2 | 12/2007 | Steiner |
| 7,326,247 | B2 | 2/2008 | Schmieding et al. |
| 7,329,281 | B2 | 2/2008 | Hays et al. |
| 7,338,492 | B2 * | 3/2008 | Singhatat ........... A61B 17/1714 128/898 |
| 7,357,803 | B2 | 4/2008 | Singhatat |
| 7,407,512 | B2 | 8/2008 | Bojarski et al. |
| 7,763,071 | B2 | 7/2010 | Bianchi et al. |
| 8,333,802 | B2 | 12/2012 | Dougherty |
| 8,491,652 | B2 | 7/2013 | Fening et al. |
| 8,535,377 | B2 | 9/2013 | Myers et al. |
| 9,011,533 | B2 | 4/2015 | Gadikota et al. |
| 2001/0021875 | A1 | 9/2001 | Enzerink et al. |
| 2002/0007182 | A1 | 1/2002 | Kim |
| 2002/0040241 | A1 | 4/2002 | Jarvinen |
| 2002/0055780 | A1 | 5/2002 | Sklar |
| 2003/0171810 | A1 | 9/2003 | Steiner |
| 2003/0171811 | A1 | 9/2003 | Steiner et al. |
| 2005/0096743 | A1 | 5/2005 | Schmieding et al. |
| 2006/0095130 | A1 | 5/2006 | Caborn et al. |
| 2006/0229722 | A1 | 10/2006 | Bianchi et al. |
| 2007/0239275 | A1 | 10/2007 | Willobee |
| 2008/0051887 | A1 | 2/2008 | Carter et al. |
| 2008/0119929 | A1 | 5/2008 | Schmieding et al. |
| 2010/0049319 | A1 | 2/2010 | Dougherty |
| 2010/0249930 | A1 | 9/2010 | Myers |
| 2014/0243978 | A1 | 8/2014 | Beck, Jr. et al. |

OTHER PUBLICATIONS

Bach, et al., Single-Incision Endoscopic Anterior Cruciate Ligament Reconstruction Using Patellar Tendon Autograft, The American Journal of Sports Medicine, 1998, 26(1):30-40.

Caborn, et al., Single Femoral Socket Double-Bundle Anterior Cruciate Ligament Reconstruction Using Tibialis Anterior Tendon: Description of a New Technique, Arthroscopy: The Journal of Arthroscopic and Related Surgery, 2005, 21(10):1273.e1-1273.e8.

Duquin, et al., Current Trends in Anterior Cruciate Ligament Reconstruction, J. Knee Surg., 2009, 22(1):7-12.

Fu, et al., Primary Anatomic Double-Bundle Anterior Cruciate Ligament Reconstruction, A Preliminary 2-Year Prospective Study, The American Journal of Sports Medicine, 2008, 36(7):1263-1274.

Georgoulis, et al., Tibial Rotation is Not Restored After ACL Reconstruction with a Hamstring Graft, Clinical Orthopaedics and Related Research, 2006, 454:89-94.

Gill, et al., Anterior Cruciate Ligament Reconstruction, The Two-Incision Technique, Orthop. Clin. N. Am., 2002, 33(4):727-735.

Jomha, et al., Long Term Osteoarthritic Changes in Anterior Cruciate Ligament Reconstructed Knees, Clinical Orthopaedics and Related Research, 1999, 358:188-193.

Milano, et al., Comparison Between Different Femoral Fixation Devices for ACL Reconstruction with Doubled Hamstring Tendon Graft: A Biomechanical Analysis, Arthroscopy: The Journal of Arthroscopic and Related Surgery, 2006, 22(6):660-668.

Pinczewski, et al., A Five-Year Comparison of Patellar Tendon Versus Four-Strand Hamstring Tendon Autograft for Arthroscopic Reconstruction of the Anterior Cruciate Ligament, The American Journal of Sports Medicine, 2002, 30(4):523-536.

Ristanis, et al., Follow-up Evaluation 2 Years After ACL Reconstruction with Bone-Patellar Tendon-Bone Graft Shows that Excessive Tibial Rotation Persists, Clin. J. Sport Med., 2006, 16(2):111-116.

Schachter, et al., Soft-Tissue Reconstruction of the Anterior Cruciate Ligament with the AperFix System, Operative Techniques in Sports Medicine, 2009, 17:57-61.

Schachter, et al., Single-Tunnel Double-Bundle Anterior Cruciate Ligament Reconstruction, Techniques in Knee Surgery, 2009, 8(2):110-114.

Seon, et al., Comparison of Single- and Double-Bundle Anterior Cruciate Ligament Reconstructions in Restoration of Knee Kinematics and Anterior Cruciate Ligament Forces, The American Journal of Sports Medicine, 2010, 38(7):1359-1367.

Yasuda, et al., Anatomic Reconstruction of the Anteromedial and Posterolateral Bundles of the Anterior Cruciate Ligament Using Hamstring Tendon Grafts, Arthroscopy: The Journal of Arthroscopic and Related Surgery, 2004, 20(10)1015-1025.

Depuy Mitek, Bio-Intrafix, Tibial Soft Tissue Fasteners, Data Sheet, 2007, 1 page.

Cayenne Medical, Inc., AperFix System Removal Technique Guide, 2008, 8 pages.

Cayenne Medical, Inc., The AperFix II System Surgical Technique Guide, A Complete Anatomic Solution, 2011, 6 pages.

PCT International Search Report and Written Opinion, PCT/US2009/060466, Apr. 12, 2010.

* cited by examiner

SINGLE TUNNEL, DOUBLE BUNDLE ANTERIOR CRUCIATE LIGAMENT RECONSTRUCTION USING BONE-PATELLAR TENDON-BONE GRAFTS

CROSS-REFERENCES TO RELATED APPLICATIONS

This application is a divisional application of U.S. Ser. No. 13/122,845 filed Apr. 6, 2011, which is a national phase of PCT International Application PCT/US2009/060466 filed Oct. 13, 2009, which claims priority from U.S. Patent Application 61/104,876 filed Oct. 13, 2008, all of which are incorporated herein by reference for all purposes.

STATEMENT REGARDING FEDERALLY SPONSORED RESEARCH

Not Applicable.

BACKGROUND OF THE INVENTION

1. Field of the Invention

The invention relates to methods and devices for ligament reconstruction in a joint. More particularly, the invention relates to a method and an implant to anatomically reconstruct the two bundles of the anterior cruciate ligament in a single femoral and tibial tunnel using a bone-patellar tendon-bone graft.

2. Description of the Related Art

There is a high prevalence of traumatic anterior cruciate ligament (ACL) injuries both in athletic and non-athletic population. ACL reconstruction is commonly performed to replace the injured ACL. However, osteoarthritis and knee pain have been reported among patients who had an ACL reconstruction 20 surgery. (See, Aglietti et al., "Long term study of anterior cruciate ligament reconstruction for chronic instability using the central one-third patellar tendon and a lateral extraarticular tenodesis" *Am J Sports Med.* 1992; 20:38-45; Jomha et al., "Long-term osteoarthritic changes in anterior cruciate ligament reconstructed knees" *Clin Orthop Relat Res.* 1999; 188-193; and Pinczewski et al., "A five-year 25 comparison of patellar tendon versus four-strand hamstring tendon autograft for arthroscopic reconstruction of the anterior cruciate ligament" *Am J Sports Med.* 2002; 30:523-536). Improving ACL reconstruction techniques that may restore normal knee stability and prevent joint degeneration remains a subject of continuing debate in sports medicine research.

Single bundle AOL reconstruction has been adopted by many surgeons. However, studies have shown that single bundle ACL reconstruction fails to restore tibial rotation to the intact level. (See, Georgoulis et al., "Tibial rotation is not restored after ACL reconstruction with a hamstring graft" *Clin Orthop Relat Res.* 2007; 454:89-94; and Ristanis et al., "Follow-up evaluation 2 years after ACL reconstruction with bone-patellar tendon-bone graft shows that excessive tibial rotation persists" *Clin J Sport Med.* 2006; 16:111-116). These observations are attributed to the limitation of single bundle ACL reconstruction to reproduce both the functional bundles (anteromedial (AM) and posterolateral (PL)) of the ACL. In order to address this issue, double tunnel-double bundle ACL reconstruction was introduced to reconstruct the two functional bundles of the ACL. There is no consensus among the studies in literature showing a significant advantage of this technique over the conventional single bundle ACL reconstruction. Although the double tunnel-double bundle ACL reconstruction technique is capable of reproducing the two functional bundles, it is a technically challenging procedure. The double tunnel-double bundle ACL reconstruction is also associated with an increase in the duration of surgery and higher cost as compared to the traditional single bundle ACL reconstruction. (See, Caborn et al., "Single femoral socket double-bundle anterior cruciate ligament reconstruction using tibialis anterior tendon: description of a new technique" *Arthroscopy* 2005; 21:1273; and Yasuda et al., "Anatomic reconstruction of the anteromedial and posterolateral bundles of the anterior cruciate ligament using hamstring tendon grafts" *Arthroscopy* 2004; 20:1015-1025). In addition, the double tunnel-double bundle ACL reconstruction makes a revision surgery difficult. By drilling two tunnels, there is an elevated risk of bone bridge damage due to an excessive loss of bone. These limitations in the current designs of the ACL reconstruction techniques leave a large scope for an improvement to this surgery.

Therefore, there is a need for improved methods and improved devices for anterior cruciate ligament reconstruction.

SUMMARY OF THE INVENTION

The present invention provides a dramatic improvement to current ACL reconstruction techniques. This invention is designed to achieve an anatomically accurate double bundle ACL reconstruction by using a single femoral and tibial tunnel. In the invention, there has been developed a method and an implant to anatomically reconstruct the two bundles of the ACL in a single femoral and tibial tunnel using a bone-patellar tendon-bone graft.

The bone-patellar tendon-bone graft is split longitudinally to form the two bundles of the ACL. The graft could be split from one end to the other forming two separated bundles or 3 to 4 centimeters of the graft could be split on both ends of the graft leaving the graft attached at the intermediate section, as described further below.

ACL reconstruction using the implant can be performed either by single incision or double incision techniques (See, Bach et at, "Single-incision endoscopic anterior cruciate ligament reconstruction using patellar tendon autograft. Minimum two-year follow-up evaluation" *Am J Sports Med.* 1998; 26(1):30-40; Gill et al., "Anterior cruciate ligament reconstruction the two-incision technique" *Orthop Clin North Am.* 2002; 33(4):127-735). The femoral and tibial tunnels are placed in a standard fashion as in the case of single bundle ACL reconstruction. The fixation plates of the implant described in detail below are attached to the four bone blocks of the split bone-patellar tendon-bone graft via sutures.

Double bundle ACL reconstruction can be achieved by fixing the ends of the graft in the femoral and tibial tunnels by placing the interference screws between the fixation plates. Graft bundles are rotated until an anatomic orientation is achieved before fixing the graft in the tunnels.

The implant of the present invention enables an accurate anatomical reconstruction of the AM and PL bundles by creating a single femoral and tibial tunnel as opposed to creating two tunnels in the tibia and femur. The surgical procedure to use this implant is related to single bundle ACL reconstruction that is currently being used by majority of surgeons. Hence, ACL reconstruction using this implant could be performed with great ease by any surgeon practicing single bundle ACL reconstruction. A revision surgery could be performed with fewer complications than double tunnel-double bundle ACL reconstruction.

In one aspect, the invention provides an implant for ligament reconstruction in a joint. The implant includes a ligament replacement having a first strand, a second strand, a first bone block, and a second bone block. The first strand and the second strand are spaced apart at a first end section of the ligament replacement, and the first strand and the second strand are spaced apart at a second opposite end section of the ligament replacement. The first bone block is attached to the first strand at the first end section of the ligament replacement, and the second bone block is attached to the second strand at the first end section of the ligament replacement. A first fixation device is positioned between the first bone block and the second bone block. The first bone block, the second bone block, and the first fixation device are dimensioned such that the first fixation device presses an outer surface of the first bone block against an inner surface of a tunnel in a first bone of the joint and presses an outer surface of the second bone block against the inner surface of the tunnel in the first bone of the joint when the first fixation device is positioned between the first bone block and the second bone block.

The ligament replacement can include a third bone block attached to the first strand of the ligament replacement at the second end section of the ligament replacement, and a fourth bone block attached to the second strand of the ligament replacement at the second end section of the ligament replacement. A second fixation device can be positioned between the third bone block and the fourth bone block. The third bone block, the fourth bone block, and the second fixation device are dimensioned such that the second fixation device presses an outer surface of the third bone block against an inner surface of a tunnel in a second bone of the joint and presses an outer surface of the fourth bone block against the inner surface of the tunnel in the second bone of the joint when the second fixation device is positioned between the third bone block and the fourth bone block.

In one form, the first fixation device includes (i) a first fixation plate and a second fixation plate spaced apart from the first fixation plate, and (ii) a first interference screw positioned between the first fixation plate and the second fixation plate of the first fixation device. The first fixation plate of the first fixation device contacts the first interference screw and an inner surface of the first bone block when the first fixation device is positioned between the first bone block and the second bone block, and the second fixation plate of the first fixation device contacts the first interference screw and an inner surface of the second bone block when the first fixation device is positioned between the first bone block and the second bone block.

In one form, the second fixation device includes (i) a third fixation plate and a fourth fixation plate spaced apart from the third fixation plate, and (ii) a second interference screw positioned between the third fixation plate and the fourth fixation plate of the second fixation device. The third fixation plate of the second fixation device contacts the second interference screw and an inner surface of the third bone block when the second fixation device is positioned between the third bone block and the fourth bone block, and the fourth fixation plate of the second fixation device contacts the second interference screw and an inner surface of the third bone block when the second fixation device is positioned between the third bone block and the fourth bone block.

The first fixation plate and the second fixation plate of the first fixation device can be integral. Alternatively, the first fixation plate and the second fixation plate of the first fixation device are not connected. The first fixation plate of the first fixation device can be sutured to an inner surface of the first bone block, and the second fixation plate of the first fixation device can be sutured to an inner surface of the second bone block.

The third fixation plate and the fourth fixation plate of the second fixation device can be integral. Alternatively, the third fixation plate and the fourth fixation plate of the second fixation device are not connected. The third fixation plate of the second fixation device can be sutured to an inner surface of the third bone block, and the fourth fixation plate of the second fixation device can be sutured to an inner surface of the fourth bone block.

Any of the fixation plates can include one or more ribs on their outer surface for engaging an inner surface of the associated bone block. Any of the fixation plates can include one or more throughholes for receiving a suture. An inner wall of the first fixation plate and an inner wall of the second fixation plate of the first fixation device can be tapped to engage threads of the first interference screw. An inner wall of the third fixation plate and an inner wall of the fourth fixation plate of the second fixation device can be tapped to engage threads of the second interference screw. Any of the fixation plates can include a first end and a opposite second end wherein an inner wall of the fixation plate is thicker adjacent the first end of the fixation plate than adjacent the second end of the fixation plate.

In one form, the first strand and the second strand are connected at an intermediate section of the ligament replacement. In another form, the first strand and the second strand are not connected. The first strand and the second strand can be selected from a patellar tendon, a hamstring tendon, an Achilles tendon, or a tibialis tendon. In yet another form, the ligament replacement is a bone-patellar tendon-bone graft split on both ends of the graft.

The tunnel in the first bone and the tunnel in the second bone can be prepared by a single incision anterior cruciate ligament reconstruction technique. Alternatively, the tunnel in the first bone and the tunnel in the second bone can be prepared by a two incision anterior cruciate ligament reconstruction technique.

In one use of the implant, the first bone is the femur, the second bone is the tibia, and the ligament is the anterior cruciate ligament. In another use of the implant, the first bone is the femur, the second bone is the tibia, and the ligament is the posterior cruciate ligament.

In another aspect, the invention provides a method for ligament reconstruction in a joint. In the method, a ligament replacement having a first strand, a second strand, a first bone block, a second bone block, a third bone block, and a fourth bone block is obtained. The first strand and the second strand are spaced apart at a first end section of the ligament replacement, and the first strand and the second strand are spaced apart at a second opposite end section of the ligament replacement. The first bone block is attached to the first strand at the first end section of the ligament replacement, the second bone block is attached to the second strand at the first end section of the ligament replacement, the third bone block is attached to the first strand of the ligament replacement at the second end section of the ligament replacement, and the fourth bone block is attached to the second strand of the ligament replacement at the second end section of the ligament replacement. The ligament replacement can be obtained by splitting a first end of a bone-patellar tendon-bone graft longitudinally to form one end of the first strand, one end of the second strand, the first bone block, and the second bone block, and splitting a second end of the bone-patellar tendon-bone graft longitudinally to form an opposite end of the first strand, an opposite end of the second strand, the third bone block, and the fourth bone block.

A first fixation device is positioned between the first bone block and the second bone block, and a second fixation device is positioned between the third bone block and the fourth bone block. A first tunnel is formed in a first bone of the joint, and a second tunnel is formed in a second bone of the joint. The first bone block, the second bone block, and the first fixation device are located in the first tunnel, and the outer dimension of the first fixation device is adjusted such that the first fixation device presses an outer surface of the first bone block against an inner surface of the first tunnel and presses an outer surface of the second bone block against the inner surface of the first tunnel. The third bone block, the fourth bone block, and the second fixation device are located in the second tunnel, and the outer dimension of the second fixation device is adjusted such that the second fixation device presses an outer surface of the third bone block against an inner surface of the second tunnel and presses an outer surface of the fourth bone block against the inner surface of the second tunnel. In one use of the method, the first bone is the femur, the second bone is the tibia, and the ligament being reconstructed is the anterior cruciate ligament.

The first fixation device can include a first fixation plate, a second fixation plate spaced apart from the first fixation plate, and a first interference screw. The second fixation device can include a third fixation plate, a fourth fixation plate spaced apart from the third fixation plate, and a second interference screw. The step of adjusting the outer dimension of the first fixation device can comprise driving the first interference screw between the first fixation plate and the second fixation plate such that the first fixation plate presses the outer surface of the first bone block against the inner surface of the first tunnel and the second fixation plate presses the outer surface of the second bone block against the inner surface of the first tunnel. The step of adjusting the outer dimension of the second fixation device can comprise driving the second interference screw between the third fixation plate and the fourth fixation plate such that the third fixation plate presses the outer surface of the third bone block against the inner surface of the second tunnel and the fourth fixation plate presses the outer surface of the fourth bone block against the inner surface of the second tunnel.

The step of positioning the first fixation device between the first bone block and the second bone block can include suturing the first fixation plate of the first fixation device to the first bone block, and suturing the second fixation plate of the fixation device to the second bone block. The step of positioning the second fixation device between the third bone block and the fourth bone block can include suturing the third fixation plate of the second fixation device to the third bone block, and suturing the fourth fixation plate of the second fixation device to the fourth bone block.

In the method, the first fixation device can be rotated until an anatomic orientation of the first strand and the second strand is achieved before driving the first interference screw between the first fixation plate and the second fixation plate. Likewise, the second fixation device can be rotated until an anatomic orientation of the first strand and the second strand is achieved before driving the second interference screw between the third fixation plate and the fourth fixation plate.

In one version of the method, the first interference screw and the second interference screw are driven in substantially the same direction. In another version of the method, the first interference screw and the second interference screw are driven in substantially opposite directions. The steps of forming the first tunnel in the first bone of the joint and forming the second tunnel in the second bone of the joint can comprise preparing the first tunnel in the first bone and the second tunnel in the second bone by a two incision anterior cruciate ligament reconstruction technique. The steps of forming the first tunnel in the first bone of the joint and forming the second tunnel in the second bone of the joint can comprise preparing the first tunnel in the first bone and the second tunnel in the second bone by a single incision anterior cruciate ligament reconstruction technique.

These and other features, aspects, and advantages of the present invention will become better understood upon consideration of the following detailed description, drawings, and appended claims.

BRIEF DESCRIPTION OF THE DRAWINGS

Like reference numerals will be used to refer to like parts from Figure to Figure in the following description of the drawings.

DETAILED DESCRIPTION OF THE INVENTION

Figure 1:
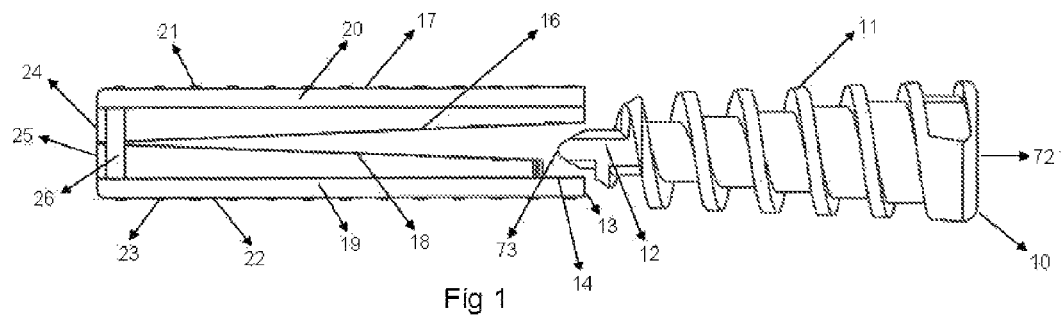
FIG. 1 shows a side view schematic of a fixation device of an implant according to the invention including two fixation plates and an interference screw.
Figure 2:
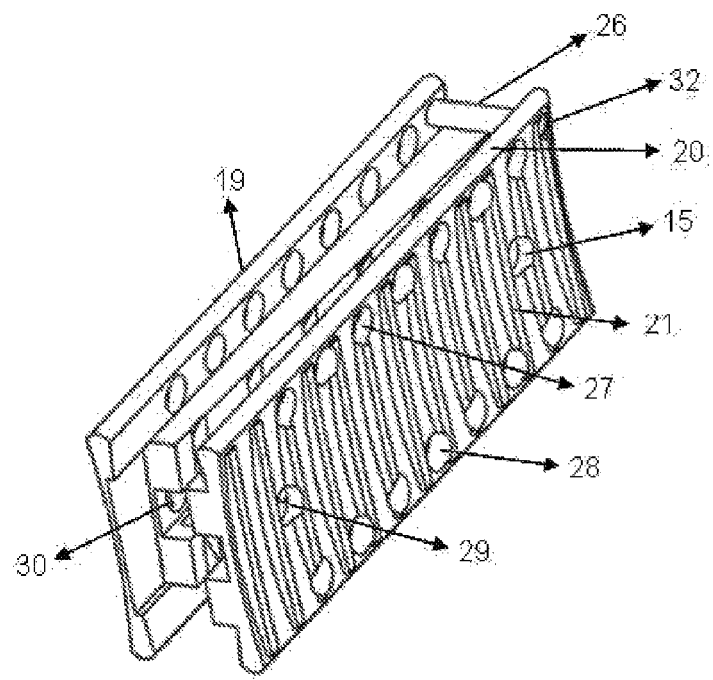
FIG. 2 shows a detailed perspective view of the fixation plates of the fixation device of FIG. 1.

The invention is capable of fixing the two graft bundles in the anatomic positions of anteromedial and posterolateral bundles by placing a single femoral and tibial tunnel. This anterior cruciate ligament reconstruction is a minimally invasive surgery that can be performed arthroscopically. Although the description of the invention is targeted towards anterior cruciate ligament reconstruction, the present invention could potential be adapted for, but not limited to, posterior cruciate ligament reconstruction and other ligament reconstructions in various joints. Anterior cruciate ligament reconstruction using the present invention can be accomplished by surgeons who are familiar with single bundle ACL reconstruction.

Embodiments of the invention feature two implants 69, 78 and a bone-patellar tendon-bone graft 68 to reconstruct the two bundles of the ACL. In one version of the invention, the bone-patellar tendon-bone graft 68 can be obtained by removing the central portion of the patient's patellar tendon using a scalpel and motorized tool. The ends of the patellar tendon are attached to bone blocks from the patient's patella and tibia. First implant 69 includes fixation plates 19, 20 and an interference screw 10. The second implant features similar fixation plates 60, 61 and an interference screw 47 as in the first implant 69. In one of the forms, the bone-patellar tendon-bone graft 68 is split from one end to the other and used with the implants 69, 78. In other embodiment, the bone-patellar tendon-bone graft 68 is split only by 3 to 4 centimeters on either ends leaving the intermediate section 46 intact and fixed with the implants 69, 78 in the tibial tunnel 65 and femoral tunnel 66. The architecture of only the first implant 69 is described in detail below since both the implants 69, 78 have the same architecture in the example embodiment.

Referring to FIGS. 1-5, the first implant 69 includes two fixation plates 19, 20 and an interference screw 10. The outer walls 17, 22 of the fixation plates 19, 20 include rib like protrusions 21, 23 to prevent any slippage between the first and second bone blocks 38, 42 and the fixation plates 19, 20. Throughholes 27 running from outer wall 17 to the inner wall 71 are present on one side of the fixation plate 20 to attach the bone blocks 38 of the bone-patellar tendon-bone graft 68 via sutures 57. Throughholes 28 running from outer wall 17 to the inner wall 71 are present on an opposite side of the fixation plate 20 to attach the bone blocks 38 of the bone-patellar tendon-bone graft 68 via sutures 57. Fixation plate 19 has throughholes 33 running from the outer wall 22 to the inner wall 70 on one side of the fixation plate 19 to attach the bone block 42 of the bone-patellar tendon-bone graft 68 via sutures 56. Fixation plate 19 has throughholes 34 running from the outer wall 22 to the inner wall 70 on an opposite side of the fixation plate 19 to attach the bone block 42 of the bone-patellar tendon-bone graft 68 via sutures 56.

Throughholes 29, 30 are present on the fixation plates 20, 19 respectively to pass strands of sutures 48, 51 used to apply tension to the graft 68. Throughholes 45, 15 are present on the fixation plates 19, 20 respectively to pass strands of sutures 100, 101 that will be used to apply tension to the graft 68 while using a single incision ACL reconstruction technique. The inner walls 16, 18 of the fixation plates 20, 19 respectively have a variable thickness to match the variable diameter of the interference screw 10 (see FIG. 1). This prevents the fixation plates 19, 20 from collapsing at the posterior ends 24, 25 and helps to maintain a desired separation between the graft bundles 40, 44.

Referring to FIG. 1, the interference screw 10 includes threads 11 that run along the entire length of the screws 10. The diameter of the interference screw 10 is larger at the anterior end 72 than the diameters at the posterior end 73. The interference screws 10 and the fixation plate 19 include a flat cut 12, 14 at the posterior end 73 and anterior end 13 respectively to allow easy insertion of the interference screws 10 between the fixation plates 19, 20.

Figure 3:
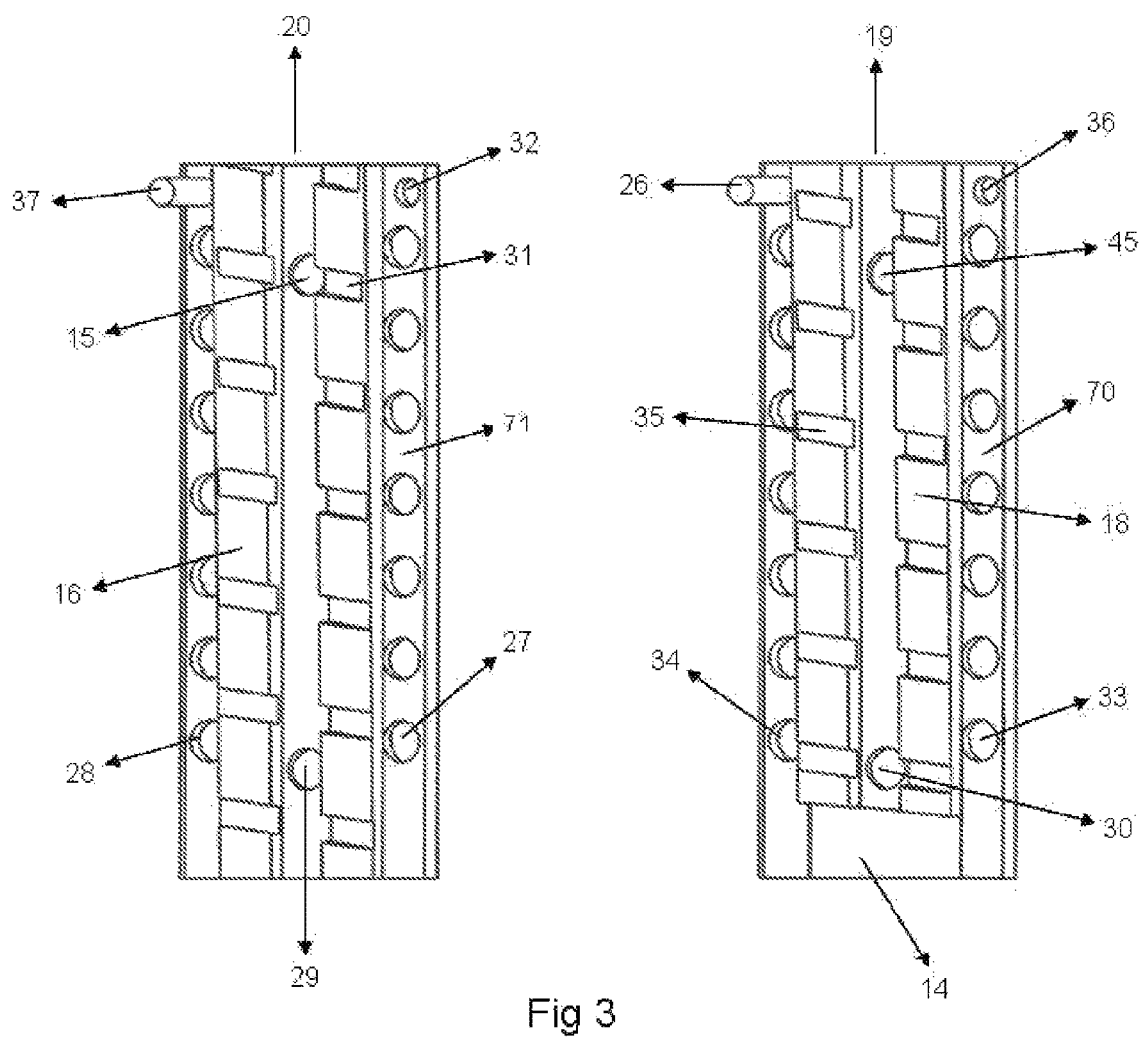
FIG. 3 shows the inner wall architecture of the two fixation plates of FIGS. 1 and 2.
Figure 4:
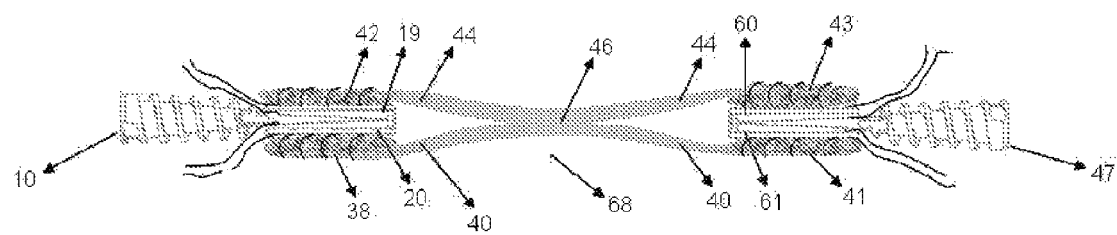
FIG. 4 shows a schematic of a bone-patellar tendon-bone graft split into two bundles on either ends with the intermediate section attached and both the ends fixed onto the fixation plates via sutures in accordance with the invention.
Figure 5:
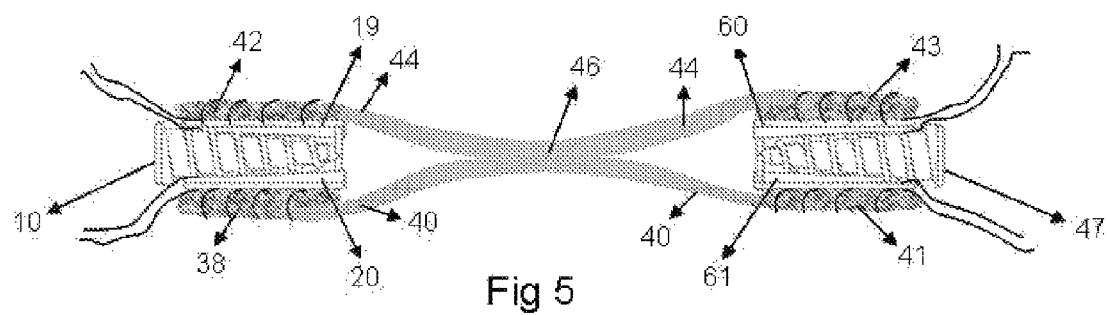
FIG. 5 shows a perspective view of the bone-patellar tendon-bone graft with the fixation plates attached after the interference screw is inserted in between them in accordance with the invention.

Referring to FIG. 3, the inner walls 16, 18 of the fixation plates 19, 20 are tapped 31, 35 to accommodate the threads 11 of the interference screws 10. Protrusions 26 and 37 are inserted into the throughholes 32 and 36 respectively to attach the fixation plates 19, 20 together before the interference screw 10 is inserted between the inner walls 16, 18 of the fixation plates 19, 20.

Referring to FIGS. 4-7, a bone-patellar tendon-bone autograft or allograft 68 is preferred for reconstructing the functional bundle of the ACL. However, other graft materials such as hamstring tendon, Achilles tendon or tibialis tendon can also be used with the present invention. The bone-patellar tendon-bone graft 68 is split longitudinally by an oscillating saw either the entire length of the graft 68, or by 3 to 4 centimeters on both of the ends of the graft 68 as preferred by the surgeon to form two graft bundles 40, 44.

Figure 10:
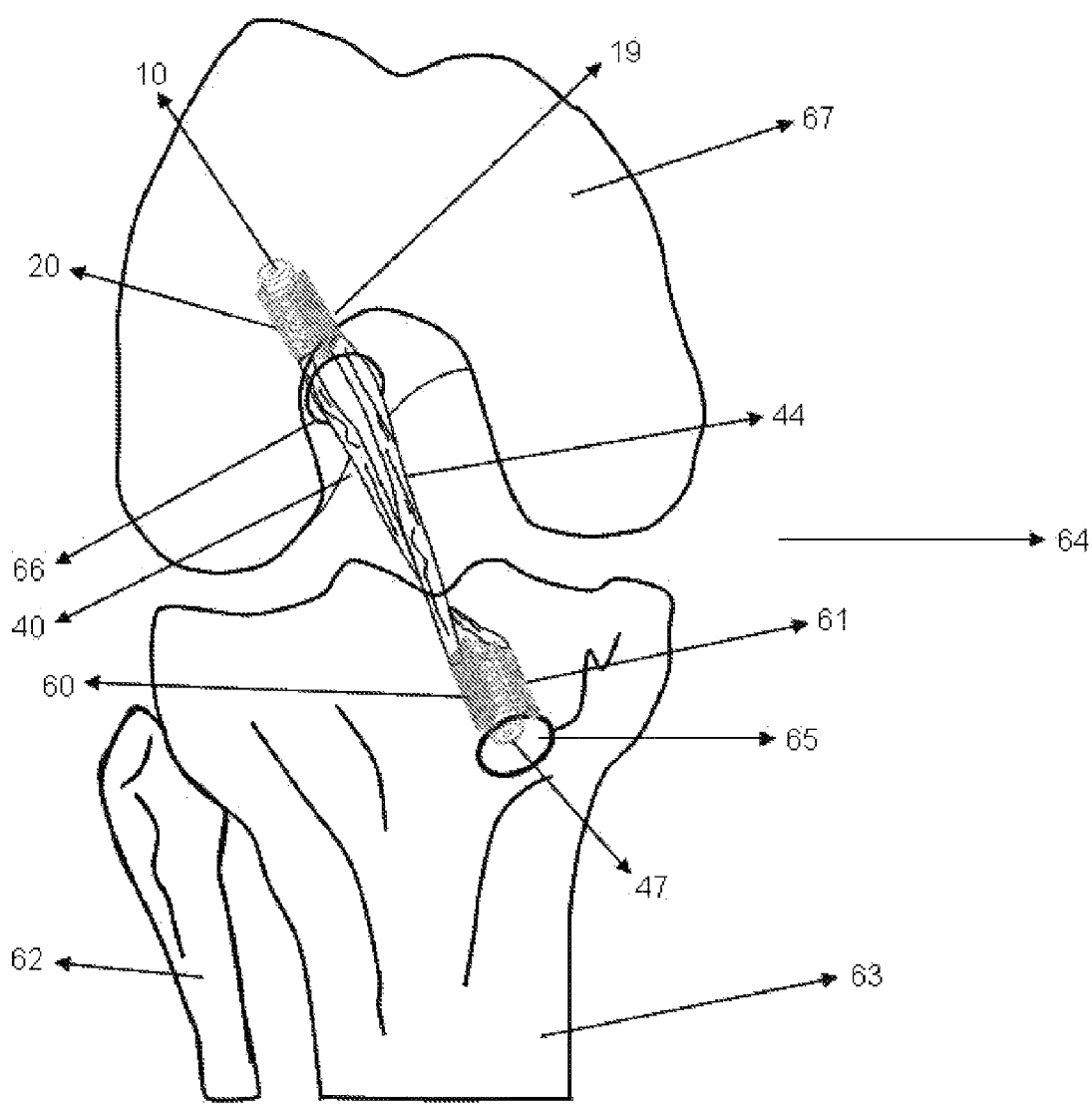
FIG. 10 shows a perspective view of an anatomical reconstruction of the ACL that reproduces the positioning of anteromedial and posterolateral bundles using the bone-patellar tendon-bone graft of FIG. 7.

Referring to FIG. 10, a schematic of the knee joint 64 is shown with femur 67, tibia 63 and fibula 62. The tibial tunnel 65 and the femoral tunnel 66 are prepared in standard fashion either by single incision or double incision ACL reconstruction techniques.

Figure 6:
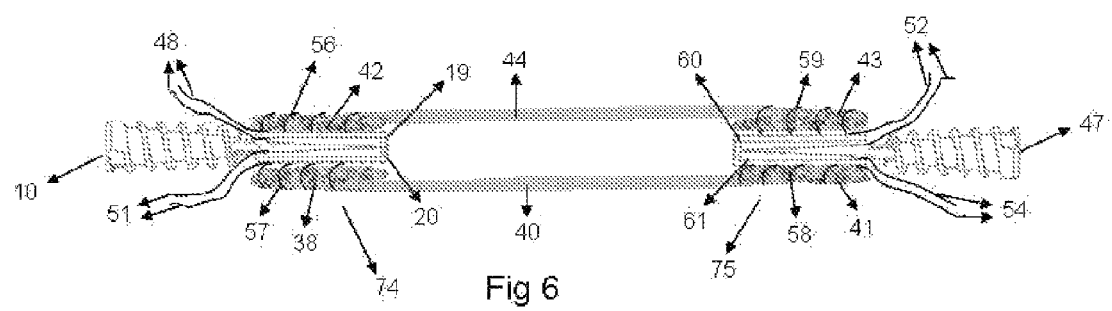
FIG. 6 shows a schematic of a bone-patellar tendon-bone graft split into two bundles from one end to the other, with the ends fixed onto the fixation plates via sutures in accordance with the invention.
Figure 7:
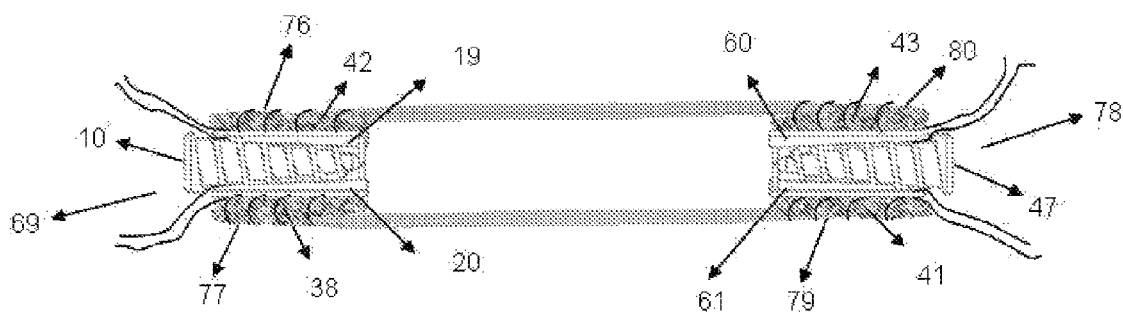
FIG. 7 shows a schematic of the bone-patellar tendon-bone graft with the fixation plates attached after the interference screw is inserted in between them in accordance with the invention.
Figure 8:
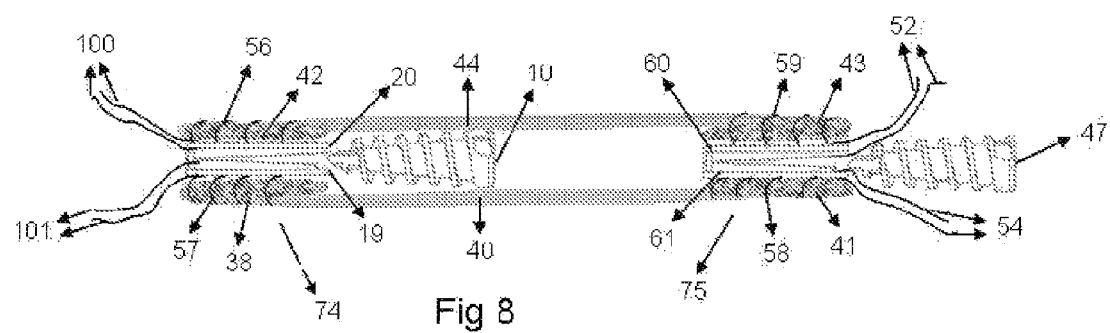
FIG. 8 shows a schematic of a bone-patellar tendon-bone graft attached to the fixation plates of the implants as used in single incision ACL reconstruction technique in accordance with the invention.
Figure 9:
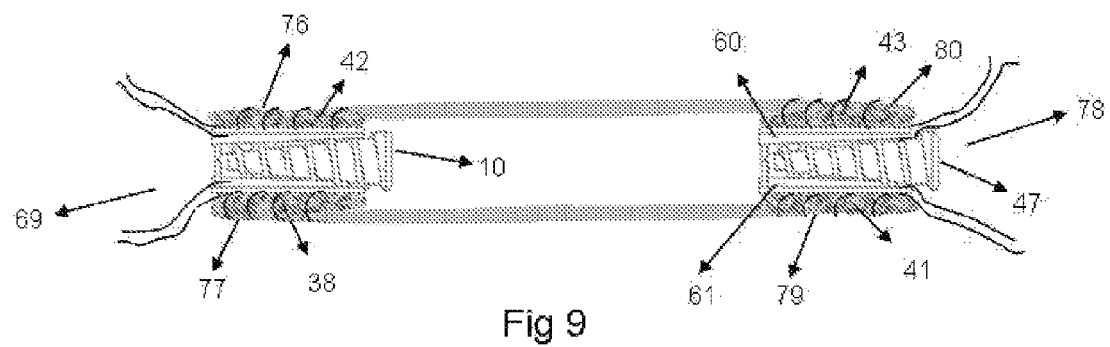
FIG. 9 shows a schematic of the bone-patellar tendon-bone graft with the fixation plates attached after the interference screw is inserted in between them as used in single incision ACL reconstruction technique in accordance with the invention.

Referring to FIG. 6-7, an example embodiment of implants 69, 78 according to the invention for ligament reconstruction is shown. The implant 69 includes a ligament replacement 68 having a first end section 74, and a second end section 75. The ligament replacement 68 includes a first strand 44 and a second strand 40. The first strand 44 and the second strand 40 are spaced apart at the first end section 74 of the ligament replacement 68. The first strand 44 and the second strand 40 are spaced apart at the second end section 75 of the ligament replacement 68. The ligament replacement 68 can comprise a patellar tendon, a hamstring tendon, an Achilles tendon, or a tibialis tendon autograft or allograft.

Implant 69 includes a first fixation plate 19 and a second fixation plate 20 spaced apart from the first fixation plate 19. The first fixation plate 19 and the second fixation plate 20 are shown as separate components; however, they could be formed integrally. Implant 69 also includes an interference screw 10 inserted between the first fixation plate 19 and the second fixation plate 20 of the first implant 69. The first fixation plate 19 of the implant 69 contacts the interference screw 10 and a surface of the first bone block 42 when the implant 69 is positioned between the first bone block 42 and the second bone block 38. The second fixation plate 20 of the implant 69 contacts the interference screw 10 and a surface of the second bone block 38 when the implant 69 is positioned between the first bone block 42 and the second bone block 38. Suture 56 connects the first fixation plate 19 of the implant 69 to the first bone block 42, and suture 57 connects the second fixation plate 20 of the implant 69 to the second bone block 38.

The first implant 69 is positioned between the first bone block 42 and the second bone block 38. When the fixation device 69 is positioned between the first bone block 42 and the second bone block 38, the implant 69 presses an outer surface 76 of the first bone block 42 against an inner surface of a tunnel 66 in the femur 67 of the knee joint 64, and the implant 69 presses an outer surface 77 of the second bone block 38 against the inner surface of the tunnel 66 in the femur 67 of the knee joint 64.

A second implant 78 is positioned between the third bone block 43 and the fourth bone block 41. When the implant 78 is positioned between the third bone block 43 and the fourth bone block 41, the implant 78 presses an outer surface 80 of the third bone block 43 against an inner surface of a tunnel 65 in the tibia 63 of the knee joint 64 and the implant 78 presses an outer surface 79 of the fourth bone block 41 against an inner surface of the tunnel 65 in the tibia 63 of the knee joint 64.

The implant 78 includes a first fixation plate 60 and a second fixation plate 61 spaced apart from the first fixation plate 60. The first fixation plate 60 and the second fixation plate 61 are shown as separate components; however, they could be formed integrally. The implant 78 also includes an interference screw 47 inserted between the first fixation plate 60 and the second fixation plate 61 of the implant 78. The first fixation plate 60 of the implant 78 contacts the interference screw 47 and a surface of the third bone block 43 when the implant 78 is positioned between the third bone block 43 and the fourth bone block 41. The second fixation plate 61 of the implant 78 contacts the interference screw 47 and a surface of the fourth bone block 41 when the implant 78 is positioned between the third bone block 43 and the fourth bone block 41. Suture 59 connects the first fixation plate 60 of the implant 78 to the third bone block 43, and suture 58 connects the second fixation plate 61 of the implant 78 to the fourth bone block 41.

Sutures 48, 51 will be used to pass the first bone block 42 and the second bone block 38 attached to the fixation plates 19, 20 respectively through the tunnel 65 in the tibia 63 and placed into the tunnel 66 of the femur 67 for double incision ACL reconstruction technique. For single incision technique, sutures 100, 101 will be used to pass the first bone block 42 and the second bone block 38 attached to the fixation plates 19, 20 respectively through the tunnel 65 in the tibia 63 and placed into the tunnel 66 of the femur 67. The two strands 40, 44 are rotated until an anatomic orientation is achieved before the interference screw 10 is inserted between the fixation plates 19, 20 of the implant 69. A first insert (interference screw 10) is then inserted by a driver between the first fixation plate 19 and the second fixation plate 20 of the implant 69. As the interference screw 10 is driven toward the posterior ends 24, 25 of the fixation plates 19, 20, the fixation plates 19, 20 move away from each other thereby pressing the outer surface 76 of the first bone block 42 against an inner surface of a tunnel 66 in the femur 67 of the knee joint 64 and pressing the outer surface 77 of the second bone block 38 against the inner surface of the tunnel 66 in the femur 67 of the knee joint 64. The first bone block 42 and the second bone block 38 heal against the tunnel 66 in the femur 67 ("bone to bone" healing). The third bone block 43 and the fourth bone block 41 attached to the fixation plates 60, 61 respectively are placed into the tunnel 66 in the tibia 63. The two strands 40, 44 are oriented anatomically before the interference screw 47 is inserted between the fixation plates 60, 61 of the implant 78. While applying an axial graft tension of 40 N through the sutures 52, 54, a second insert (interference screw 47) is inserted by a driver between the first fixation plate 60 of the second implant 78 and the second fixation plate 61 of the second implant 78. As the interference screw 47 is driven toward the posterior ends of the fixation plates 60, 61, the fixation plates 60, 61 move away from each other thereby pressing the outer surfaces of the third bone block 43 and the fourth bone block 41 against the inner surface of the tunnel 65 in the tibia 63. The third bone block 43 and the fourth bone block 41 heal against the tunnel 65 in the tibia 63 ("bone to bone" healing).

Thus, the invention provides methods and devices for ligament reconstruction in a joint. More particularly, the invention provides a method and an implant to anatomically reconstruct the two bundles of the anterior cruciate ligament in a single femoral and tibial tunnel using a bone-patellar tendon-bone graft.

Although the present invention has been described in detail with reference to certain embodiments, one skilled in the art will appreciate that the present invention can be practiced by other than the described embodiments, which have been presented for purposes of illustration and not of limitation. Therefore, the scope of the claims should not be limited to the embodiments described herein.

What is claimed is:

1. A method for ligament reconstruction in a joint, the method comprising:

providing a ligament replacement having a first strand comprising a first bone block, a second strand comprising a second bone block, the first strand and the second strand being split apart at a first end section and at a second opposite end section of the ligament replacement, the first bone block being attached to the first strand at the first end section of the ligament replacement, and the second bone block being attached to the second strand at the first end section of the ligament replacement;

positioning a fixation device between the first bone block and the second bone block;

forming a first tunnel in a first bone of the joint;

forming a second tunnel in a second bone of the joint;

locating the first bone block, the second bone block, and the fixation device in the first tunnel;

adjusting an outer dimension of the fixation device such that the fixation device is configured to press an outer surface of the first bone block against an inner surface of the first tunnel and the fixation device is configured to press an outer surface of the second bone block against the inner surface of the first tunnel; and anchoring the second end section of the ligament replacement in the second tunnel.

2. The method of claim 1 wherein:

the fixation device includes a first fixation plate, a second fixation plate spaced apart from the first fixation plate, and an interference screw, and the step of adjusting the outer dimension of the fixation device comprises driving the interference screw between the first fixation plate and the second fixation plate such that the first fixation plate presses the outer surface of the first bone block against the inner surface of the first tunnel and the second fixation plate presses the outer surface of the second bone block against the inner surface of the first tunnel.

3. The method of claim 2 wherein:

the step of positioning the fixation device between the first bone block and the second bone block comprises suturing the first fixation plate of the fixation device to the first bone block, and suturing the second fixation plate of the fixation device to the second bone block.

4. The method of claim 3 wherein:

the step of adjusting the outer dimension of the fixation device comprises rotating the fixation device until an anatomic orientation of the first strand and the second strand is achieved before driving the interference screw between the first fixation plate and the second fixation plate.

5. The method of claim 2 wherein:

the ligament replacement further comprises a third bone block attached to the first strand of the ligament replacement at the second end section of the ligament replacement, and a fourth bone block attached to the second strand of the ligament replacement at the second end section of the ligament replacement;

the step of anchoring the second end section of the ligament replacement in the second tunnel comprises positioning a second fixation device between the third bone block and the fourth bone block, and adjusting an outer dimension of the second fixation device such that the second fixation device presses an outer surface of the third bone block against an inner surface of the second tunnel and presses an outer surface of the fourth bone block against the inner surface of the second tunnel.

6. The method of claim 5 wherein:

the second fixation device includes a third fixation plate, a fourth fixation plate spaced apart from the first fixation plate, and a second interference screw, and the step of anchoring the second end section of the ligament replacement in the second tunnel further comprises driving the second interference screw between the third fixation plate and the fourth fixation plate such that the third fixation plate presses the outer surface of the third bone block against the inner surface of the second tunnel and the fourth fixation plate presses the outer surface of the fourth bone block against the inner surface of the second tunnel.

7. The method of claim 6 wherein:

the step of anchoring the second end section of the ligament replacement in the second tunnel further comprises feeding a suture through a throughhole in at least one of the third fixation plate and the fourth fixation plate, pulling the second fixation device in a direction away from the first tunnel and thereafter driving the second interference screw between the third fixation plate and the fourth fixation plate.

8. The method of claim 6 wherein:

the interference screw and the second interference screw are driven in substantially the same direction.

9. The method of claim 6 wherein:

the interference screw and the second interference screw are driven in substantially opposite directions.

10. The method of claim 1 wherein:

the steps of forming the first tunnel in the first bone of the joint and forming the second tunnel in the second bone of the joint comprise preparing the first tunnel in the first bone and the second tunnel in the second bone by two incision anterior cruciate ligament reconstruction technique.

11. The method of claim 1 wherein:

the steps of forming the first tunnel in the first bone of the joint and forming the second tunnel in the second bone of the joint comprise preparing the first tunnel in the first bone and the second tunnel in the second bone by single incision anterior cruciate ligament reconstruction technique.

12. The method of claim 2 wherein:

the first bone is the femur;

the second bone is the tibia; and the ligament being reconstructed is the anterior cruciate ligament.

13. The method of claim 2 wherein:

the step of providing the ligament replacement comprises splitting an end of a bone-patellar tendon-bone graft longitudinally to form the first strand, the second strand, the first bone block, and the second bone block.

* * * * *

UNITED STATES PATENT AND TRADEMARK OFFICE
CERTIFICATE OF CORRECTION

PATENT NO. : 9,770,323 B2  
APPLICATION NO. : 14/690851  
DATED : September 26, 2017  
INVENTOR(S) : Hemanth R. Gadikota et al.

Page 1 of 1

It is certified that error appears in the above-identified patent and that said Letters Patent is hereby corrected as shown below:

In the Specification

Column 1, Line 46, "127" should be --727--.

Column 9, Line 50, "66" should be --65--.

Signed and Sealed this  
Twenty-sixth Day of December, 2017

Joseph Matal  
*Performing the Functions and Duties of the*  
*Under Secretary of Commerce for Intellectual Property and*  
*Director of the United States Patent and Trademark Office*